(12) United States Patent
Matsumoto

(10) Patent No.: US 11,141,070 B2
(45) Date of Patent: Oct. 12, 2021

(54) HEART FAILURE EVALUATION METHOD AND DIAGNOSIS DEVICE

(71) Applicant: Teijin Pharma Limited, Tokyo (JP)

(72) Inventor: Sadayoshi Matsumoto, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 760 days.

(21) Appl. No.: 15/327,048

(22) PCT Filed: Jul. 22, 2015

(86) PCT No.: PCT/JP2015/071424
§ 371 (c)(1),
(2) Date: Jan. 18, 2017

(87) PCT Pub. No.: WO2016/013684
PCT Pub. Date: Jan. 28, 2016

(65) Prior Publication Data
US 2017/0164840 A1    Jun. 15, 2017

(30) Foreign Application Priority Data
Jul. 22, 2014 (JP) .............................. JP2014-149263

(51) Int. Cl.
*A61B 5/02* (2006.01)
*A61B 5/0205* (2006.01)
(Continued)

(52) U.S. Cl.
CPC ................ *A61B 5/02* (2013.01); *A61B 5/021* (2013.01); *A61B 5/0205* (2013.01);
(Continued)

(58) Field of Classification Search
CPC ..... A61B 5/02; A61B 5/0205; A61B 5/02055; A61B 5/021; A61B 5/024; A61B 5/02405;
(Continued)

(56) References Cited

U.S. PATENT DOCUMENTS 7,433,853 B2    10/2008    Brockway et al.
8,301,232 B2 *  10/2012    Albert .................. A61B 5/0006
                                                                600/509

(Continued)

FOREIGN PATENT DOCUMENTS

EP    1102196 A2     5/2001
JP    50-128387 A   10/1975
(Continued)

OTHER PUBLICATIONS

Communication, dated Apr. 1, 2019, issued by the Chinese Patent Office in counterpart Chinese Patent Application No. 201580039483.9.

(Continued)

*Primary Examiner* — Ahmed M Farah
(74) *Attorney, Agent, or Firm* — Sughrue Mion, PLLC

(57) ABSTRACT

Provided are a means to detect a plurality of dynamics, a processing unit that calculates a temporal change in the detected dynamics, and an evaluation device that determines exacerbation of clinical conditions in heart failure of a patient based on the calculated change in the patient's dynamics over time. The present invention makes it possible to detect, early and with high accuracy, that the onset of acute heart failure is imminent.

15 Claims, 4 Drawing Sheets

(51) Int. Cl.
*A61B 5/145* (2006.01)
*A61B 5/00* (2006.01)
*A61B 5/091* (2006.01)
*G16H 50/30* (2018.01)
*A61B 5/08* (2006.01)
*A61B 5/024* (2006.01)
*A61B 5/021* (2006.01)
*A61B 5/029* (2006.01)
*A61B 10/00* (2006.01)

(52) U.S. Cl.
CPC .......... *A61B 5/02007* (2013.01); *A61B 5/029* (2013.01); *A61B 5/02028* (2013.01); *A61B 5/02405* (2013.01); *A61B 5/08* (2013.01); *A61B 5/0816* (2013.01); *A61B 5/091* (2013.01); *A61B 5/14542* (2013.01); *A61B 5/4035* (2013.01); *A61B 5/7275* (2013.01); *A61B 10/00* (2013.01); *G16H 50/30* (2018.01); *A61B 5/7264* (2013.01); *A61B 2505/07* (2013.01)

(58) Field of Classification Search
CPC ....... A61B 5/0245; A61B 5/08; A61B 5/0803; A61B 5/0816; A61B 5/091; A61B 5/0935; A61B 5/40; A61B 5/4035; A61B 5/4058; A61B 5/4076; A61B 5/72; A61B 5/7232; A61B 5/7271; A61B 5/7275; A61B 5/02028; A61B 5/7282; A61B 5/7285; A61B 5/7289; A61B 5/7292
USPC ........ 600/301, 481, 483–485, 515–518, 529, 600/533, 538
See application file for complete search history.

(56) References Cited

U.S. PATENT DOCUMENTS

| | | | | |
|---|---|---|---|---|
| 8,301,252 B2* | 10/2012 | Hatlestad | ............. | A61B 5/7475 607/27 |
| 8,403,865 B2 | 3/2013 | Halperin et al. | | |
| 9,375,566 B2* | 6/2016 | Stahmann | ............. | G16H 20/30 |
| 2005/0085734 A1 | 4/2005 | Tehrani | | |
| 2005/0090753 A1 | 4/2005 | Goor et al. | | |
| 2006/0135999 A1* | 6/2006 | Bodner | ............. | A61N 1/36514 607/4 |
| 2008/0157980 A1 | 7/2008 | Sachanandani et al. | | |
| 2010/0298899 A1* | 11/2010 | Donnelly | ............. | A61N 1/37258 607/6 |
| 2011/0077616 A1* | 3/2011 | Bennett | ................ | A61B 5/0215 604/503 |
| 2011/0301435 A1* | 12/2011 | Albert | ................ | A61B 5/0404 600/301 |
| 2012/0232416 A1* | 9/2012 | Gilham | ................ | A61B 5/7246 600/515 |
| 2013/0116578 A1 | 5/2013 | An et al. | | |
| 2014/0194705 A1 | 7/2014 | Kwok et al. | | |
| 2014/0330139 A1* | 11/2014 | Banet | ................ | A61B 5/0205 600/484 |
| 2014/0336491 A1* | 11/2014 | Balda | ................ | A61B 5/02438 600/384 |
| 2014/0350361 A1 | 11/2014 | De Chazal et al. | | |
| 2014/0364706 A1 | 12/2014 | Schindhelm et al. | | |
| 2017/0188961 A1* | 7/2017 | Banet | ................ | A61B 5/6892 |
| 2017/0281097 A1* | 10/2017 | Thakur | ................ | A61B 5/7282 |

FOREIGN PATENT DOCUMENTS

| | | |
|---|---|---|
| JP | 2004-527296 A | 9/2004 |
| JP | 2009-517187 A | 4/2009 |
| JP | 2010-508128 A | 3/2010 |
| JP | 2010-514498 A | 5/2010 |
| JP | 2014-64951 A | 4/2014 |
| WO | 2010/091168 A1 | 8/2010 |

OTHER PUBLICATIONS

Teruo Takano, "New concept of heart failure and progress of disease management", The Journal of Japan Society for Clinical Anesthesia, 1996, vol. 16, No. 4, pp. 326-332 (8 pages total).

Communication dated Jan. 30, 2018, issued by the Japanese Patent Office in counterpart application No. 2016-536011.

International Search Report of PCT/JP2015/071424, dated Oct. 20, 2015.

Communication, dated Mar. 13, 2018, issued by the European Patent Office in counterpart EP Patent Application No. 15824273.5.

* cited by examiner

HEART FAILURE EVALUATION METHOD AND DIAGNOSIS DEVICE

CROSS REFERENCE TO RELATED APPLICATIONS

This is a U.S. national stage of application No. PCT/JP2015/071424, filed on Jul. 22, 2015. Priority under 35 U.S.C.§ 119(a) and 35 U.S.C.§ 365(b) is claimed from Japanese Patent Application No. 2014-149263 filed on Jul. 22, 2014, the disclosure of which is incorporated herein by reference.

TECHNICAL FIELD

The present invention relates to an evaluation method to detect that the onset of acute heart failure is imminent and to a diagnosis device thereof.

BACKGROUND ART

Heart failure is a syndrome resulting from a falling of the heart pumping function. There are a wide variety of causes and clinical conditions accompanied with symptoms such as dyspnea, breath shortness, oliguresis, edema at the four limbs and hepatomegaly. When the heart pumping function rapidly falls and symptoms suddenly emerge, the heart failure is named "acute heart failure". When the acute heart failure is at the stage in which the overall physical status is stable, it is called "chronic heart failure". More particularly, acute heart failure is defined as "a clinical condition of rapid emergence or exacerbation of signs and symptoms secondary to increased ventricular end-diastolic pressure and decreased perfusion of major organs, which are caused by acute loss of compensation mechanism of the pumping function of the heart due to its organic and/or functional abnormalities (Guidelines for Treatment of Acute Heart Failure-2011 revised edition)". Chronic heart failure is defined as "a clinical condition of pulmonary congestion and systemic venous congestion with impairment of everyday life functions caused at the stage when the heart pumping function decreases due to chronic myocardial impairment and lack of absolute or relative ejection of blood volume to balance with the oxygen demand of the peripheral major organs (Guidelines for Treatment of Chronic Heart Failure (2005 revised edition)". The repetition of "acute heart failure" and "chronic heart failure" is one of the characteristics of heart failure in general, and treatment according to each clinical condition is required.

FIG. 2 is a diagram conceptually illustrating the repetition of "acute heart failure" and "chronic heart failure". As shown in FIG. 2, when acute heart failure develops for the first time (t1), a cardiac function falls by a degree of only $\delta 1$ compared to that before the onset, the cardiac function recovers to some extent after passing the duration of $\tau 1$ over time, and clinical conditions are stabilized and acute heart failure shifts to chronic heart failure. Even though the clinical conditions appear to be stable, chronic heart failure progresses, and after passing the duration of SP1, a compensatory mechanism rapidly fails, resulting in the second acute heart failure (t2). Generally, the falling of cardiac function by a degree of $\delta 2$ at this time becomes greater than that of cardiac function $\delta 1$ when acute heart failure developed for the first time, and the condition becomes more serious. In addition, the duration of $\tau 2$ required for recovery of cardiac function gets longer compared to E1, the duration required for the first recovery. Furthermore, the degree of recovery of the cardiac function often becomes low relative to the degree of recovery from the first acute heart failure (cardiac function after shifting to a stable state SP1). Furthermore, a stable state SP2 is often shorter than the stable state SP1, so the third event of acute heart failure is more likely to develop relatively sooner than the previous cases. In other words, signs described in FIG. 2 become $\delta 1 < \delta 2 < \delta 3$ ..., $\tau 1 < \tau 2 < \tau 3$ ..., SP1>SP2>SP3> ....

Thus, when acute heart failure develops, gradually more time is required for the recovery of the cardiac function, and the degree of recovery tapers off. Furthermore, the frequency of developing acute heart failure also increases gradually. For these reasons, it is quite important not to develop acute heart failure. In order to do so, a method to evaluate the conditions of heart failure of a patient is disclosed in PTL1, wherein an index of change in conditions of heart failure which represents information on the change in the condition of heart failure of the patient is determined, based on data indicating the conditions of the patient obtained from a non-contact sensor.

In addition, in the explanation of the present specification, the statement about clinical conditions and the progresses of chronic heart failure is made for a typical case, and clinical conditions and progresses that are different from this explanation may appear in individual patients with chronic heart failure.

The present invention is intended to provide a diagnosis device that can properly diagnose by taking into account that the clinical conditions and developments may be different depending on the individual patient with chronic heart failure.

CITATION LIST

Patent Literature

[PTL 1]
 Japanese Unexamined Patent Application Publication No. 2014-064951
[PTL 2]
 Japanese Translation of PCT International Application Publication No. JP-T-2010-508128
[PTL 3]
 Japanese Translation of PCT International Application Publication No. 2004-527296
[PTL 4]
 Japanese Unexamined Patent Application Publication No. 50-128387

SUMMARY OF INVENTION

Technical Problem

The purpose of the present invention is to provide an evaluation method and a diagnosis device that can detect changes in clinical conditions of a patient with heart failure, at an early stage with high accuracy in predicting acute heart failure developments.

Solution to Problem

The first present invention is a diagnosis device for chronic heart failure, wherein a medical professional observes changes in clinical condition of a patient with chronic heart failure and uses the device for diagnosis, comprising: one or more detection means for continuously detecting one or a plurality of different physiological indexes of the patient, and a means for generating information to generate and output information that the medical professional uses for observation and/or diagnosis on the basis of one or more of the physiological indexes, wherein the means for generating information is constituted so that at least one aspect of the following (1) to (4) is made different between the first observation period and the second observation period:
(1) selection of each of the physiological indexes used for generating the information
(2) order of priority of each of the physiological indexes used for generating the information
(3) weighting of each of the physiological indexes used for generating the information
(4) determination threshold of each of the physiological indexes used for generating the information In other words, the diagnosis device of the first present invention comprises two observation modes, wherein the first observation mode corresponds to the first observation period, and the second observation mode corresponds to the second observation period.

Herein, the first observation mode is suitable for assessing a state in which a compensatory mechanism is functioning (or seems to function) with the goal of improving clinical conditions resulting from the falling of the heart pumping function of the patient, and the second observation mode is a suitable for assessing a state in which the compensatory mechanism has failed (or seems to have failed).

The second present invention is a diagnosis device for chronic heart failure, wherein a medical professional observes changes of clinical conditions of a patient with chronic heart failure in whom the compensatory mechanism is suspected to be functioning, and uses the device for diagnosis, wherein the compensatory mechanism aims at improving various clinical conditions due to the falling of the heart pumping function, comprising a means for generating information to generate and output information for prediction and/or diagnosis on the basis of the detected information of a physiological index, including at least one of (a) augmentation state of the sympathetic nervous system, (b) state of vasoconstriction, and (c) (at least one of respiratory frequency, an index indicating respiratory stability, or the amount of ventilation) of the patient.

The third present invention is a diagnosis device for chronic heart failure, wherein a medical professional observes changes of clinical conditions of a patient with chronic heart failure and uses the device for diagnosis, comprising: one or more detection means to continuously detect one or a plurality of different physiological indexes of the patient, and a means for generating information to generate and output information that the medical professional uses for observation and/or diagnosis on the basis of one or more of the detected physiological indexes, wherein the means for generating information is constituted so that at least one aspect of the following (1) to (4) is different according to one or more of progressive stage of chronic heart failure, the severity and background diseases of the patient:
(1) selection of each of the physiological indexes used for generating the information
(2) order of priority of each of the physiological indexes used for generating the information
(3) weighting of each of the physiological indexes used for generating the information
(4) determination threshold of each of the physiological indexes used for generating the information The fourth present invention is a diagnosis device for chronic heart failure, wherein a medical professional observes changes in clinical conditions of a patient with chronic heart failure and uses the device for diagnosis, comprising: a plurality of detection means for continuously detecting a plurality of different physiological indexes of the patient, and a means for generating information to generate and output information that the medical professional uses for observation and/or diagnosis on the basis of a plurality of the physiological indexes, wherein the means for generating information is constituted to generate information based on the indexes including at least (I) (at least one of respiratory frequency, an index indicating respiratory stability, and the amount of ventilation) and (II) an index indicating the augmentation state of the sympathetic nervous system.

The fifth present invention is a diagnosis device for chronic heart failure, wherein a medical professional observes changes in clinical conditions of a patient with chronic heart failure and uses the device for diagnosis, comprising: a plurality of detection means for continuously detecting a plurality of different physiological indexes of the patient, and a means for generating information to generate and output information that the medical professional uses for observation and/or diagnosis on the basis of a plurality of the physiological indexes, wherein the means for generating information is constituted to generate information based on the indexes including at least (I) (at least one of respiratory frequency, an index indicating respiratory stability, and the amount of ventilation) and (III) cardiac output.

The sixth present invention is a diagnosis device for chronic heart failure, wherein a medical professional observes changes in clinical conditions of a patient with chronic heart failure and uses the device for diagnosis, comprising: a plurality of detection means for continuously detecting a plurality of different physiological indexes of the patient, and a means for generating information to generate and output information that the medical professional uses for observation and/or diagnosis on the basis of a plurality of the physiological indexes, wherein the means for generating information is constituted to generate information based on the indexes including at least (I) (at least one of respiratory frequency, an index indicating respiratory stability, and the amount of ventilation), (II) an index indicating the augmentation state of the sympathetic nervous system and (III) cardiac output.

The seventh present invention is a evaluation device for exacerbation of clinical conditions of heart failure comprising: a detection means for detecting a plurality of dynamics, a processing unit for calculating the temporal change in multiple dynamics obtained by the detection means, and a determination unit for determining exacerbation of clinical conditions of heart failure of a patient on the basis of temporal change in the calculated dynamics of the patient.

The eighth present invention is an evaluation method for exacerbation of clinical conditions of heart failure, comprising the steps of: obtaining a plurality of dynamics of a patient on the basis of a detection means, calculating the temporal change in these obtained dynamics, and determining exacerbation of clinical conditions of heart failure of a patient on the basis of the calculated temporal change in the patient's dynamics.

Advantageous Effects of Invention

According to the present invention, a change in clinical conditions such as exacerbation of clinical conditions of chronic heart failure can be detected with great accuracy and the compensatory mechanism failure of the patient can be predicted at an early stage. In addition, by performing more accurate and more certain follow-up treatment of chronic heart failure, such as further changes in clinical conditions of the patient who falls into a compensatory mechanism failure, it becomes possible to prevent, for example, a patient with acute heart failure from developing chronic heart failure.

REFERENCE SIGNS LIST

Figure 1:
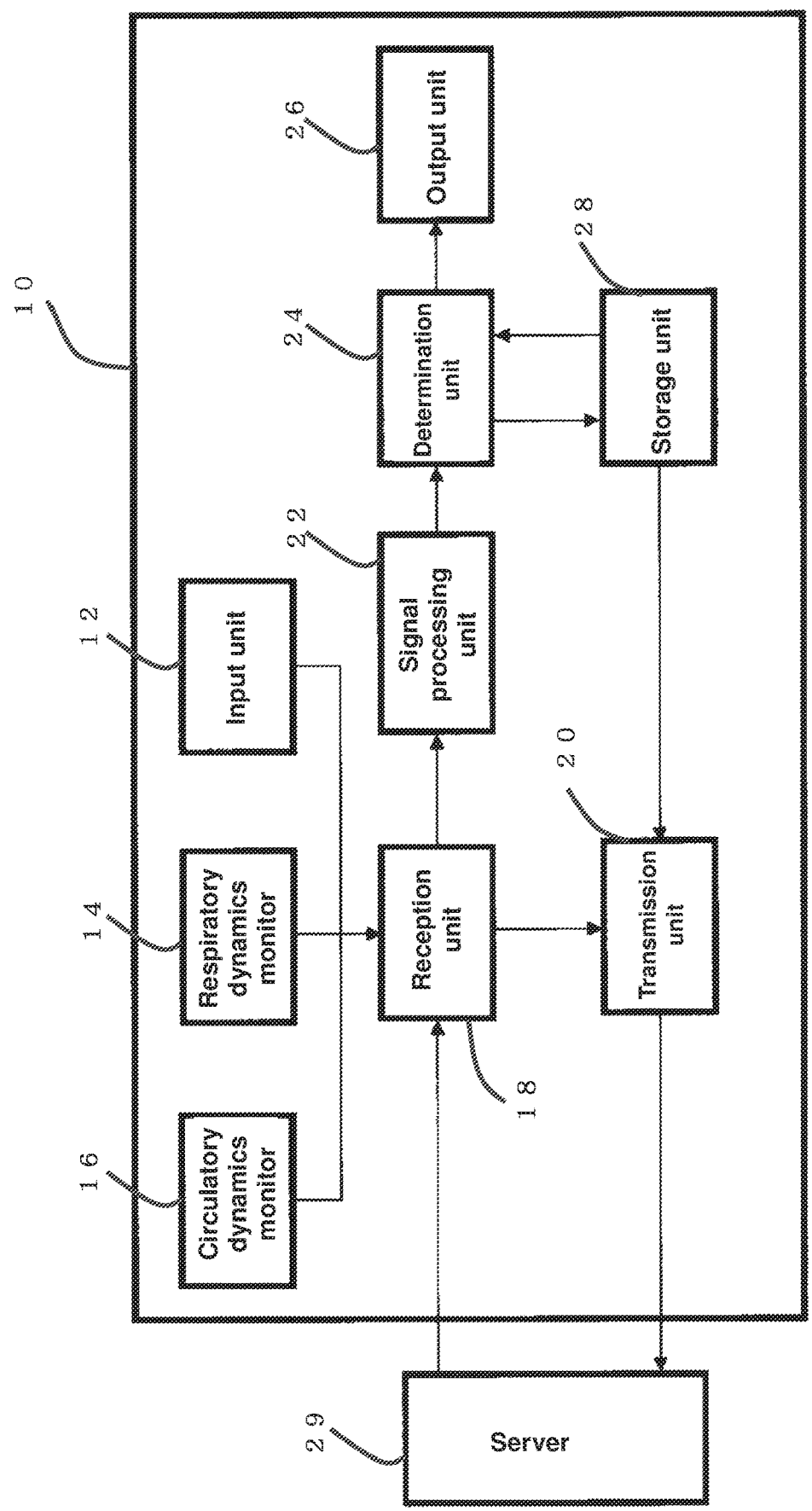
FIG. 1 is a block diagram illustrating a favorable embodiment of a diagnosis device for heart failure in the present invention.
Figure 2:
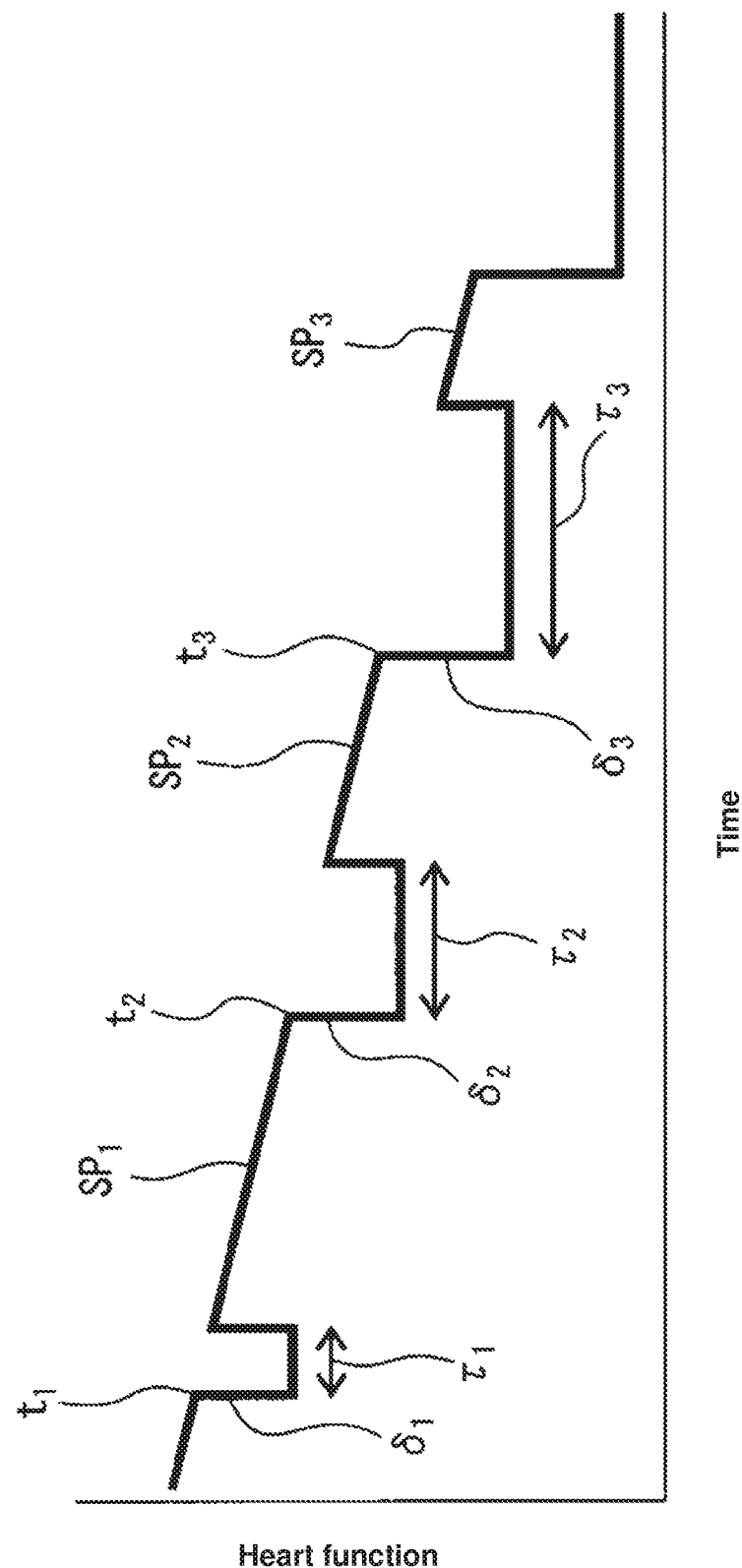
FIG. 2 is a conceptual diagram showing exacerbation of a cardiac function due to the repetition of acute heart failure and chronic heart failure.

10. Diagnosis system for heart failure
12. Input unit
14. Respiratory dynamics monitor
16. Circulatory dynamics monitor
18. Reception unit
20. Transmission unit
22. Signal processing unit
24. Determination unit
26. Output unit
28. Storage unit
29. Server
30. Early phase of heart failure
31. Management by a compensatory mechanism
32. Breakdown
40. Early stage of the observation
41. Management stage by a compensatory mechanism
42. Stage of breakdown
t: Onset of acute heart failure
δ: Fall of cardiac function at the onset of acute heart failure
τ: Time required for the recovery of cardiac function from acute heart failure
SP: Stable phase of the cardiac function
C1: Falling of the heart pumping function
C2: Pulmonary congestion
C3: Augmentation of sympathetic nerve activity
C4: Augmentation of RAS activity
C5: Vasoconstriction
C6: Arrhythmia
P1: Cardiac Output
P2: Blood pressure
P3: Oxygen saturation degree in blood (SpO2)
P4: Cardiac contractile force
P5: Heart rate
P6: Body fluid volume
P7: Body weight
P8: Respiratory frequency
P9: Pulse rate

DESCRIPTION OF EMBODIMENTS

The present invention is the same as described in the section of "the disclosure of the invention". However, a change in clinical conditions of a patient with chronic heart failure may involve a change in clinical conditions from which the occurrence of acute exacerbation is predicted in each invention.

In addition, although the present invention is constituted so that the generation of diagnostic information is different depending on whether a compensatory mechanism is functioning in chronic heart failure disease in the first present invention, or the progressive stage and the degree of severity of chronic heart failure in the third present invention. However, the diagnosis device of the present invention may be constituted so that a user, for example a medical professional, of the diagnosis device of the present invention can switch which diagnostic information is generated.

Referring to the first invention as an example, when a medical professional once decides that a compensatory mechanism is functioning in a patient with chronic heart failure, the observation is started as in the first observation period. In this state, the diagnosis device of the present invention generates diagnostic information indicating more precisely that the patient is in the state in which the compensatory mechanism is functioning. However, when this information no longer indicates that the compensatory mechanism is functioning, the medical professional can suspect that this patient with heart failure is in the state of breakdown of the compensatory mechanism. Consequently, the medical professional switches the diagnosis device of the present invention to the second observation period in which diagnostic information indicates with greater accuracy the state of breakdown of the compensatory mechanism. Accordingly, the medical professional can perform diagnostic evaluations with high certainty.

Besides, the diagnosis device of the present invention may be constituted so that the device itself switches between the first observation period and the second observation period. Furthermore, the diagnosis device may be constituted to determine whether the compensatory mechanism is functioning or not.

For example, in the beginning of the diagnosis, the compensatory mechanism is assumed to be functioning and the diagnostic information is generated as that belonging to the first observation period, but if the diagnostic information indicates the breakdown of the compensatory mechanism or the diagnostic information changes to the diagnostic information indicating the breakdown of the compensatory mechanism during the use of the diagnosis device of the present invention, the generation of the diagnostic information is started as that belonging to the second observation period, wherein execution of such switching is displayed, and diagnostic information corresponding to the second period in which the breakdown of the compensatory mechanism is more precisely shown is displayed. Subsequently, when the diagnostic information indicating the breakdown of the compensatory mechanism disappears and the functional recovery of the compensatory mechanism is indicated, the device switches back to the generation of diagnostic information corresponding to the first observation period again and displays the event.

In the second observation period, however, diagnostic information indicating further worsening of the breakdown state of the compensatory mechanism instead of the functional recovery of the compensatory mechanism may be generated.

In the diagnosis device of the present invention, both of the means for generating information, namely a means for generating diagnostic information from which the compensatory mechanism can be determined as functioning and a means for generating diagnostic information from which the compensatory mechanism can be determined as broken down are made to function based on at least part of the physiological indexes detected continuously from a patient, and the diagnosis device of the present invention may be constituted to determine comprehensively whether the compensatory mechanism is functioning or not based on the set of generated information. However, the display unit may be arranged in such a way to only display the results of determination whether the compensatory mechanism is functioning or not and the diagnostic information which accurately indicates the state of determination. For example, if the compensatory mechanism is determined as functioning, the display unit may be arranged to display the diagnostic information corresponding to the first observation period together with the results of the determination.

With reference to the attached drawings below, other favorable embodiments of the present invention are explained.

First Embodiment

In FIG. 1, a heart failure diagnosis system 10 consists of an input unit 12, a respiratory dynamics monitor 14, a circulatory dynamics monitor 16, a reception unit 18, a transmission unit 20, a signal processing unit 22, a determination unit 24, an output unit 26 and a storage unit 28 as primary components.

The input unit 12 can be constituted with a keyboard, a touch panel and others to input necessary orders to the heart failure diagnosis system 10 and edit data stored in the storage unit 28.

The respiratory dynamics monitor 14 can be constituted with a sensor, an instrument and a system that measure, for example, respiratory frequency and the amount of ventilation of a patient with heart failure, a subject for diagnosis.

Such a sensor, an instrument and a system may adopt various kinds of methods such as one to detect respiratory gas flow using a respirator equipped with a nasal mask that a patient wears, a temperature sensor or pressure sensor (such as piezoelectric sensor and the like) that are attached to the nasal cavity part of the patient; a method to detect breathing motion by the thorax movement of a patient by attaching an expandable sensor to the patient's chest; a method to detect breathing motion by changes in pressure by installing a piezoelectric sensor on a futon, a bed a pillow, and the like.

In addition, as a non-contact sensor which is different from the contact sensor described above, for example, a sensor can include a method to detect breathing by a reflection wave (Doppler signal) from a subject irradiated with an electromagnetic wave (microwave) disclosed in the Japanese Translation of PCT International Application Publication No. 2010-508128, and a high-sensitivity human sensor utilizing a reflection wave returned from an object irradiated with infrared rays, an RF motion sensor and the like.

The circulatory dynamics monitor 16 can be constituted with a sensor and an instrument that measures for example, oxygen saturation in blood (SpO2), pulse rate, blood pressure and cardiac output of a patient. Such a sensor and an instrument can include a pulse oximeter, a cardiac output monitor, preferably a noninvasive cardiac output monitor and the like.

The reception unit 18 is connected to the input unit 12, the respiratory dynamics monitor 14, the circulatory dynamics monitor 16, and the server 29 outside the system. The reception unit 18 can include a USB port and a LAN port of a computer, a bus and a bridge circuit inside the computer.

The transmission unit 20 can include a LAN port which is connected to the server 29.

The signal processing unit 22 and the determination unit 24 can be constituted with a CPU inside the computer and appropriate program.

The storage unit 28 can be constituted with RAM, a hard disk drive, SSD (Solid State Drive) of a computer and the like.

The output unit 26 can be constituted with a display or panel indicating measurement results from the respiratory dynamics monitor 14 and the circulatory dynamics monitor 16, for example, such as current respiratory frequency, the amount of ventilation, oxygen saturation in blood, pulse rate, blood pressure, cardiac output of the patient and determination results from the determination unit 24.

The effects of the present embodiments are explained as follows.

Data from the respiratory dynamics monitor 14 and circulatory dynamics monitor 16 are sent to the signal processing unit 22 via the reception unit 18, and processes such as nondimensionalization and averaging are performed in the signal processing unit 22. The data from the respiratory dynamics monitor 14 and circulatory dynamics monitor 16 may be output from the reception unit 18 to the server 29 outside of the system via the transmission unit 20 so that the data is accumulated in the server 29.

The information processed in the signal processing unit 22 is output to the determination unit 24. The determination unit 24 performs a readout of the determination criteria from the storage unit 28 and determines the current state of heart failure of a patient based on the determination criteria and the information from the signal processing unit 22. The determination results are output from the determination unit 24 to the output unit 26, and displayed in the output unit 26. The determination unit 24 also outputs information from the signal processing unit 22 to the storage unit 28. The storage unit 28 saves this as the past data relating to its measurement time. The past data may be saved in the server 29 outside of the system via the transmission unit 20.

Furthermore, for other embodiment not illustrated, the device may be constituted so that the detected physiological index is sent from the sensor which detects the above-mentioned physiological indexes to the server via a wired or wireless communication channel, analyzed, evaluated, and reporting information of the evaluated results are generated by the server. This reporting information is likewise sent to the computer of a client via a communication channel so that a medical professional confirms the determined result.

In addition, the present invention can be conducted using a well-known communication/computing system, and either one of them is within the scope of the present invention.

Generally, heart failure is associated with various types of respiratory failures. For example, when pulmonary edema due to pulmonary congestion progresses in a patient with chronic heart failure, the oxygen saturation in blood decreases because the ventilation capacity in the lungs decreases. The decrease in oxygen saturation in blood leads to the increase in respiratory frequency through a compensatory mechanism of the human body.

In addition, as an example of the mechanism explaining the increase in respiratory frequency due to pulmonary congestion, a mechanism is considered wherein a J receptor in the lungs is activated and results in the increase in respiratory frequency when an interstitial edema occurs due to pulmonary edema.

The appearance of rapid and shallow breathing is likely a symptom indicating the decrease in the ventilation capacity of the lungs. When a compensatory mechanism does not function sufficiently, the respiratory frequency further increases. Especially, when the respiratory frequency of a patient is higher in a resting state, this phenomenon conspicuously indicates a deteriorating (exacerbation) state of heart failure. In addition, for many other chronic diseases, respiratory frequency generally changes relatively slowly, such as over months or years, but for chronic heart failure, respiratory frequency may rapidly increase over hours or days.

In addition, for pulmonary congestion-related heart failure, the decrease in the ventilation capacity in the lungs leads to the decrease in the oxygen saturation in blood. Therefore, simultaneous observation of temporal changes in respiratory frequency and the oxygen saturation in blood enables a more precise detection of exacerbation of clinical conditions of heart failure.

According to the present embodiment, exacerbation of clinical conditions of heart failure can be detected in a highly precise manner, the breakdown of the compensatory mechanism of a patient can be detected at an early stage, and acute heart failure can be prevented in patients with chronic heart failure.

Second Embodiment

Figure 3:
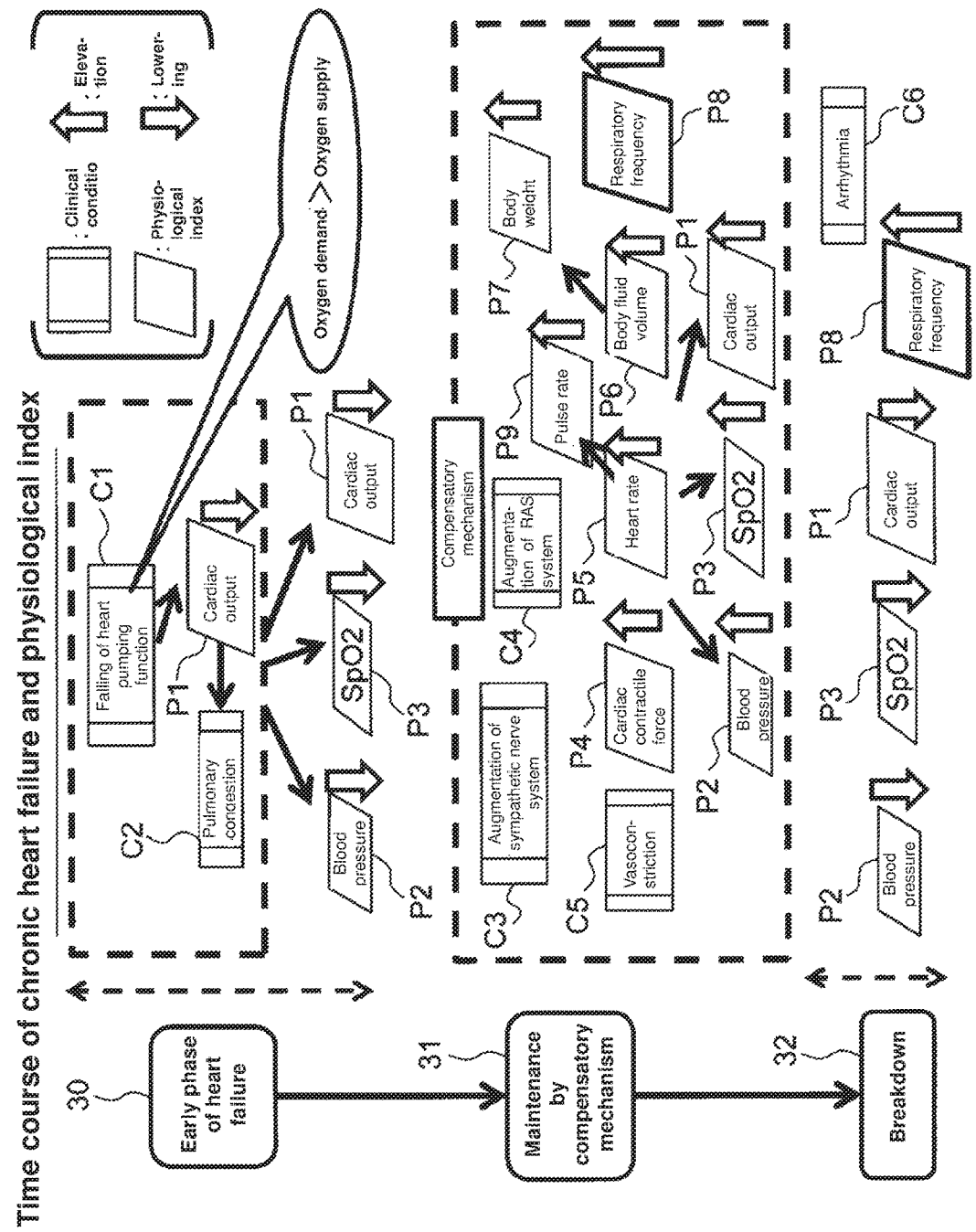
FIG. 3 is a diagram illustrating the relationship between clinical condition and physiological indexes of chronic heart failure.
Figure 4:
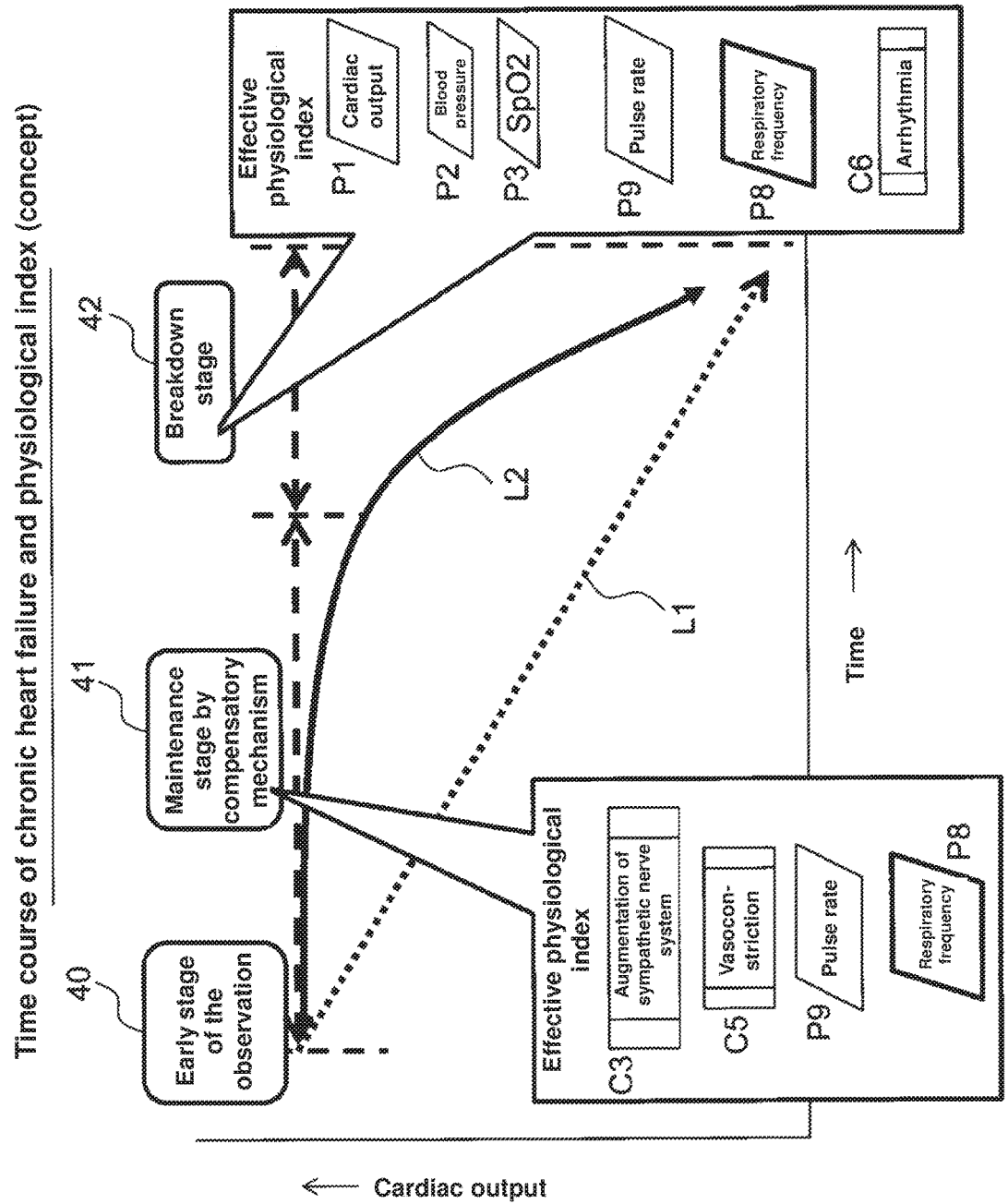
FIG. 4 is a diagram illustrating the relationship between the chronological development of chronic heart failure and a physiological index.

Next, the second embodiment is explained by another look at the present invention according to FIGS. 1, 3 and 4.

Note that the diagnosis device for heart failure used in the present embodiment follows the system 10 explained in the constitution as the first embodiment in FIG. 1, and a constitution such as the detection unit of some physiological indexes not clearly specified in the first embodiment is explained below.

I. Monitor Unit of Each Physiological Index

In the present embodiment, one or more monitor parts, which are included in the respiratory dynamics monitor 14 and the circulatory dynamics monitor 16 as shown in FIG. 1 and one including anything but those above which is used for the follow-up treatment of the patient with chronic heart failure, detect (and output if needed) the following physiological index.

(1) Monitor Unit Capturing the Augmentation of the Sympathetic Nervous System

It is known that the augmentation of the sympathetic nervous system causes a change in the interval of cardiac beats in the heart. This monitor unit captures the state of augmentation of the sympathetic nervous system by heartbeat change analysis (also called as HRV: Heart Rate Variability) which captures such a change. In addition, the augmentation state of the sympathetic nervous system may be detected by other methods. For example, heart rate P5 and pulse rate P9 may be used for this purpose, and an index detecting blood pressure or vasoconstriction is also an index to capture the augmentation state of the sympathetic nervous system.

The detection of heart rate P5 is often achieved by detecting pulse rate P9 which is approximately equivalent to P5 as an index. For explanations below, the statement "heart rate P5" means "heart rate P5 or pulse rate P9".

(2) Monitor Unit Capturing the State of Vasoconstriction

The state of vasoconstriction may be detected by an invasive method called the vascular catheterization (a method to measure the degree of tension of each part of a blood vessel of the circulatory system by measuring cardiac output and combining the results of blood pressure together), or by a method to detect the state of vasoconstriction disclosed in the U.S. Pat. No. 3,694,438, wherein blood vessel compliance is obtained by displaying Lissajous figure formed by the radius arterial blood pressure waveform and the plethysmography waveform, which is used to display and update the degree of tension of the blood vessel per heartbeat triggered by an electrocardiogram.

(3) Respiratory Frequency Monitor Unit

Similar to the explanation in the first embodiment of the present invention above, the respiratory dynamics monitor 14 can be constituted with a sensor, an instrument and a system to measure an index of respiratory frequency, the respiratory stability and the amount of ventilation of a patient with heart failure as the diagnostic subject. Such a sensor, an instrument and a system can include a respirator equipped with a nasal mask which a patient wears, and a non-contact sensor (a high sensitivity human sensor and an RF motion sensor), for example, as described in the Japanese Translation of PCT International Application Publication No. 2010-508128, using a method to detect breathing by a reflection wave (Doppler signal) from a subject irradiated with an electromagnetic wave (microwave).

The respiratory dynamics monitor 14 may adopt various kinds of methods such as a method to detect respiratory gas flow using a temperature sensor or pressure sensor (such as piezoelectric sensor and the like) that are attached to the nasal cavity part of the patient, a method to detect breathing motion by the thorax movement of a patient by attaching an expandable sensor to the patient's chest, and a method to detect breathing motion by changes in pressure by installing a piezoelectric sensor on a futon, a bed, a pillow and the like.

Based on these techniques, the respiratory frequency monitor unit in this embodiment detects respiratory frequency of the patient per predetermined time (simply called "respiratory frequency" or "respiratory rate" in the present description).

For the index of breathing dynamics, other indexes about breathing including respiratory stability or the amount of ventilation may be used besides the respiratory frequency or in addition to the above. The indexes for respiratory stability or respiratory constancy are, for example, numerical indexes of temporal change in the respiratory cycle per unit time or temporal change in the frequency of respiratory signals which are statistically processed. In the present description, the parts explained as "breathing", "respiratory rate" and "respiratory frequency" literally mean the index of "respiratory frequency" and the index including the indexes of breathing stability and constancy mentioned above and the amount of ventilation.

One of the reasons that the amount of ventilation is included as a detection index is that a sequence is also considered, wherein anoxia is induced by pulmonary edema and consequently the increase in carbon dioxide chemical hypersensitivity, the increase in respiratory frequency and/or the increase in the amount of ventilation are derived from the anoxia.

(4) Cardiac Output Monitor Unit

A cardiac output monitor unit may be constituted with a constitution which is similar to a method for calculating the cardiac output of a subject from an active component of the integral impedance for living body, for example, as disclosed in the Japanese Translation of PCT International Application Publication No. 2004-527296 and its corresponding product "Noninvasive cardiac output monitor NICaS 2004Slim" (Manufacturer: NImedical, Manufacturer: Nippon Americare Co., Ltd., nonproprietary name:

Impedance cardiac output flowmeter, medical devices approval number: 22400BZX00041000), or the monitor unit may have a function to detect cardiac output by various other invasive or noninvasive methods.

In addition, a statement is noted that in case cardiac output decreases, the sympathetic nerve system and RAA system (Renin-Angiotensin-Aldosterone System; RAAS) start to act as compensatory mechanisms, and contractile capacity increases, heart rate and intravascular volume increase besides vasoconstriction. Thus, cardiac output is elevated resulting from the increase in contractile capacity, heart rate and intravascular volume. Additionally, it is noted that cell indexes of the heart muscles (myocardial fiber such as troponin and calcium dynamics) are changeable indexes responding to the fall of the heart pumping functions, similar to pro-neurohumoral factors in the sympathetic nerve and RAA system. In addition, regardless of each stage of clinical conditions of chronic heart failure, fluid volume (congestion index of the lungs and the systemic vein, the degree of edema and body weight may be included) may be used as an effective index for a patient with heart failure and congestion.

For use of the diagnosis device for heart failure in the present embodiment, which is assumed to be mainly operated at home, the results of biochemical tests during a medical examination in a medical institution can be also utilized. Therefore, results from BNP (brain natriuretic peptides), echocardiography, X-rays, detection values from other tests as well as troponin can be used as evaluation and determination indexes of the diagnosis device for heart failure. Thus, the present embodiment is expected to be used with these various clinical and medical physiological indexes.

(5) Blood Pressure Monitoring Unit

Blood pressure is detected by various kinds of methods including the traditional noninvasive sphygmomanometer using a cuff (manchette) sensing blood pressure.

(6) Oxygen Saturation in Blood Monitoring Unit

A well-known pulse oximeter is a noninvasive diagnostic tool for measuring oxygen saturation in blood in patients based on the results obtained by calibrating the relationship between the ratio of fluctuation component of transmitted amount of light of red light (R) and the infrared radiation (IR) for the arterial blood and oxygen saturation in blood. The principle of the measurement is disclosed, for example, in published unexamined patent application No. S50-128387. Oxygen saturation in blood is detected by such a pulse oximeter or other methods.

(7) Arrhythmic State Monitoring Unit

The pulse oximeter mentioned above can simply detect a state of arrhythmia (including atrial fibrillation and extrasystole) by knowing chronological information of heartbeat motion obtained from time information corresponding to the heartbeat on a performance curve of changes in oxygen saturation in blood (the position of the peak). Arrhythmia may be also detected using an electrocardiography.

(8) Monitoring Unit for Augmentation State of RAS System

Renin-angiotensin system (RAS) or renin-angiotensin-aldosterone system (RAAS), which is a hormone-based collective term associated with the regulation of blood pressure and the extracellular volume, and is activated in accordance with hypotension and a reduction in circulatory blood volume. Therefore, the augmentation state of the RAS system can be detected by monitoring blood pressure and circulatory blood volume.

In addition, the augmentation state of the RAS system has an influence on the indexes described above such as vasoconstriction, blood pressure and body weight.

II. Findings of the Inventors Regarding Changes in Clinical Conditions of Chronic Heart Failure and Physiological Indexes Next, the finding of the inventors regarding the changes in clinical conditions of chronic heart failure and the physiological indexes that have led to creation of the diagnosis device for chronic heart failure in the second embodiment of the present invention is explained referring to FIGS. 3 and 4.

FIG. 3 is a conceptual diagram illustrating the occurrence of heart failure exacerbation phenomenon in a typical patient with chronic heart failure, various clinical conditions occurring therefrom and the changes in physiological indexes associated with them. The clinical conditions according to the progress of heart failure: 30 for "an early phase of heart failure", 31 for "maintenance by a compensatory mechanism" and 32 for "breakdown" are shown. Each clinical condition is explained in detail as follows.

(1) Early Phase of Heart Failure

Simply put, exacerbation of heart failure is a clinical condition C1, which indicates that the heart pumping function is decreased. Due to this, cardiac output P1 decreases and deterioration of circulatory dynamics often leads to pulmonary congestion C2.

In this state, since physiological oxygen demand at each site in the body exceeds the oxygen supply provided by blood circulating throughout the body, oxygen saturation in blood often decreases, blood pressure often lowers or blood flow often decreases.

(2) Maintenance by Compensatory Mechanisms

As mentioned above, because oxygen demand exceeds oxygen supply and the oxygen saturation in blood has decreased due to the exacerbation of heart failure, a chemoreceptor in a patient's body detects the decrease in the amount of oxygen and the increase in carbon dioxide in the body. In addition, a baroreceptor in the body detects a reduction in blood pressure in the same way. Furthermore, a renal artery in the body detects a reduction in blood flow resulting in augmentation of the RAS system.

In response to these detected results, body mechanisms aiming at improving the clinical conditions such as reduction in blood pressure, the decrease in a cardiac output and the decrease in the amount of oxygen are called "compensatory mechanisms".

There are multiple targets which are specifically subjected to be controlled as compensatory mechanisms. For example, there is a compensatory mechanism which aims at increasing circulatory blood flow volume per unit of time as a result of augmentation of the sympathetic nervous system C3 followed by the increase in cardiac contractile force (P4) and heart rate (P5), and the augmentation of the sympathetic nervous system C3 also results in the increase in cardiac output P1. In addition, there is a compensatory mechanism which tries to elevate the volume of blood returning to the heart through the contraction of blood vessel C5. Since the RAS system constricts blood vessels to increase the body fluid volume, the blood pressure P2 begins to increase.

In addition, similarly as a compensatory mechanism, the regulation center of the brain aims at increasing the amount of gas exchange in the lungs by raising the respiratory frequency P8.

As a result of the work of the compensatory mechanisms, when the increase in blood volume returning to the heart and the increase in the amount of gas exchange in the lungs are achieved, oxygen saturation in blood P3 begins to increase, resulting in temporary release of a distressed feeling (feeling of suffocation) of the patient.

Meanwhile, on page 9 of "Guidelines Treatment for Chronic Heart Failure" (2005 revised edition) (Japanese Circulation Society http://www.j-circ.or.jp/guideline/pdf/JCS2005_matsuzaki_d.pdf#search='%E6%85%A2%E6%80%A7%E5%BF%83%E4%B8%8D%E5%85%A8+%E4%BD%93%E9%87%8D%E5%A2%97%E5%8A%A0'), there is a statement that "body weight gain within a short period is important as an index of the fluid retention. When body weight increases more than 2 kg per day, acute exacerbation of chronic heart failure is strongly suggested." Therefore, the acute exacerbation of chronic heart failure leads to fluid retention, and as a result, sudden gain of body weight is often found. In other words, body weight P7 is an index of the amount of fluid retention.

Also, augmentation of the RAS system C4 is observed when the blood pressure and the intravascular volume decrease.

In the functional stage of the compensatory mechanism reviewed above, the physiological indexes for the observation of clinical conditions and the prediction of acute exacerbation of the patient that should be weighed particularly heavily are amenable to detection with high accuracy and treatment according to findings of the inventors. As a result, such physiological indexes are respiratory frequency P8, pulse rate P9, and HRV (Heart Rate Variability) obtained from the pulse, which can detect the breakdown of the compensatory mechanism with precision.

(3) Breakdown

When the regulation for cancellation of decrease in cardiac output, reduction in blood pressure and oxygen deficiency by the compensatory mechanism cannot catch up with the degree of falling of the heart pumping function C1, the maintenance of cardiac output, blood pressure and the amount of oxygen supply by the compensatory mechanism will break down.

As the cardiac output P1 decreases and the blood volume ejected from the heart decreases, blood pressure P2 decreases and hence the oxygen saturation in blood P3 also decreases. Furthermore, at the final stage of the falling of heart pumping function C1, arrhythmia C6 may appear and its frequency likely increases. In addition, when the sympathetic nerve system is augmented but is not at the breakdown stage, arrhythmia induced by the augmentation of the sympathetic nerve system may occur.

The sequence of change in the physiological indexes in the clinical conditions of chronic heart failure described above is explained referring to FIG. 4 from a chronological standpoint.

FIG. 4 is a diagram illustrating the relationship between the cardiac output in a typical patient with chronic heart failure (longitudinal axis) and the elapsed time (horizontal axis). The horizontal axis indicates an early phase of the observation 40 showing the maintenance stage of the compensatory mechanism 41 and the breakdown stage of the compensatory mechanism 42.

In FIG. 4, the first characteristic line L1 is drawn by assuming that a compensatory mechanism does not work. Under this condition, after exacerbation of heart failure occurs, cardiac output continuously decreases without room for recovery, resulting in the final phase of the breakdown stage.

Similarly, the second characteristic line L2 conceptually shows a case in which a compensatory mechanism is assumed to work after exacerbation of heart failure occurs. In the maintenance stage 41 by the compensatory mechanism, although cardiac output is barely maintained within the tolerance level, the cardiac output often suddenly decreases when the cardiac output enters the breakdown stage 42.

Next, from the clinical standpoint, physiological indexes that should be counted as important in each stage of clinical conditions of heart failure is explained based on the findings of the inventors.

In the maintenance stage 41 by the compensatory mechanism described in FIG. 4, the augmentation of the sympathetic nerve C3 and the like occur as a compensatory mechanism for reduction in cardiac output, lowering blood pressure and oxygen deficiency resulting in vasoconstriction C5 and the increase in heart rate P5 (pulse rate P9) as one of the consequences. Therefore, when such clinical conditions or physiological indexes are observed, it will be found that the patient is currently in the maintenance stage 41 by the compensatory mechanism. Particularly, the observation of heart rate P5, namely pulse rate P9, is easy to use as an index.

In addition, as explained earlier, in the maintenance stage 41 by the compensatory mechanism, when falling of pump function C1 progresses and the compensatory mechanism cannot catch up with it, it is expected that the increase in respiratory frequency P8 may be significant, therefore, respiratory frequency P8 is an extremely important index to determine whether the stage shifts to the breakdown stage 42 or not, i.e. as a prediction of the development of acute exacerbation.

Next, when the patient reaches breakdown stage 42, since it is evident that the compensatory mechanism is not able to catch up with that state, events such as reduction in cardiac output P1, lowering of blood pressure P2, increase in the respiratory frequency P8, and/or observation of the tendency of appearance of the arrhythmia C6 as phenomena of exacerbation of the heart failure are considered to be an evidence that the patient is progressing in the breakdown stage 42.

In addition, phenomena such as the falling of cardiac output P1, the lowering of blood pressure P2, the increase in respiratory frequency P8 and/or the progress of the degree of arrhythmia C6 can be used as prediction indexes for the approaching of the final phase of the breakdown stage 42. The increase in respiratory frequency P8 is particularly important for the reasons explained previously.

III. Regulation of the Diagnosis Device for Heart Failure in this Embodiment

Next, a characteristic regulation that the signal processing unit 22 and the determination unit 24 provided in the diagnosis device for heart failure in this embodiment is explained based on the findings by the inventors about the relationship between the clinical conditions of chronic heart failure described above and each physiological index.

In addition, on the occasion of the implementation of the present invention, a constitution may be realized by adding a new regulation based on the findings of the inventors concerning clinical conditions and the progression of chronic heart failure as explained earlier in addition to the following example, or a constitution may be realized by substituting regulations to be explained below.

In addition, notations such as "a maintenance stage by the compensatory mechanism", "a breakdown stage" are often used in the following explanation, these notations are used as a meaning of a notation including "an observation period that is suspected of being in those stages" in the explanation context for the regulation of the diagnosis device for heart failure in this embodiment.

(1) Regulation of the Maintenance Stage 41 by the Compensatory Mechanism

At this stage, the augmentation of sympathetic nerve C3 occurs as a compensatory mechanism for the reduction in cardiac output, the decrease in circulatory blood volume, lowering of blood pressure and oxygen deficiency, as one of results, vasoconstriction C5, the increase in heart rate P5 (pulse rate P9) and the increase in cardiac output P1 occur, and respiratory frequency P8 increases to compensate for the oxygen deficiency. Furthermore, the noticeable increase in the respiratory frequency P8 is often found before shifting to the breakdown stage 42. Therefore, the respiratory frequency P8 is an extremely important index to determine whether the stage shifts to the breakdown stage 42 or not, i.e. as prediction of the development of acute exacerbation.

Therefore, during the functional stage 41 of the compensatory mechanism or the observation period in which the functional stage of the compensatory mechanism is suspected to be working, one or more indexes including at least one of the augmentation stage of the sympathetic nerve C3, vasoconstriction C5, and (at least one of respiratory frequency P8, index indicating the respiratory stability and the amount of ventilation) are continuously observed, and when a significant change as stated below is found in any of them, or when a combination of them appears according to a predetermined rule, alert signals are generated so that a medical professional can observe (the situation). Or certain index values (for example these physiological indexes or index indicating the degree of risks calculated according to the predetermined rule) are generated and provided to the medical professional for observation.

The medical professional observes those index values indicating the generated alert signals and risks, and takes necessary medical procedures such as hospitalization by performing diagnoses to confirm the results. This medical intervention may include changes in types of drugs and dose.

Alternatively, when a patient and his or her family see index values indicating the alert signals and risks, they may respond to these events by going to a medical institution by themselves.

In addition, the conditions under which the signal processing unit 22 and determination unit 24 observe changes in these physiological indexes and generate alert signals, or generate index values showing risks are those cases corresponding to predetermined determination rule including the following cases, for example, where one or more physiological indexes including at least one of the augmentation state of the sympathetic nervous system, pulse rate P9, a state of vasoconstriction C5, respiratory frequency and one or more physiological indexes (at least one of respiratory frequency P8, index indicating the respiratory stability and the amount of ventilation) correspond to one or more events including one of (A) exceeding the predetermined upper limit threshold, (B) being less than the predetermined lower limit threshold, (C) exceeding the predetermined elevation limit threshold per predetermined time of period, (D) exceeding the predetermined decline limit threshold per predetermined time of period, (E) exceeding the predetermined elevation rate limit threshold, or (F) exceeding the predetermined decline rate limit threshold.

In addition, the device may be constituted to generate alert signals and index values indicating risks by using at least one piece of information about the occurrence of events (A) to (F) and the duration of those events, the number of occurrences of one or more events of (A) to (F) and the total amount of time of occurrences of one or more events of (A) to (F) within the predetermined period.

(2) Regulation of the Breakdown Stage 42

It has already been explained earlier that, when a patient has reached breakdown stage 42, since the compensatory mechanism is unable to catch up with it, there may be a case where falling of cardiac output P1, lowering of blood pressure P2 and increase in respiratory frequency P8 occur, or emergence of the onset of arrhythmia C6 may occur as phenomena of heart failure exacerbation.

Therefore, in the breakdown stage 42 in which the pump function in the heart C1 is found to be so low that the compensatory mechanism cannot catch up with it or the observation period which is suspected to be at the breakdown stage, the diagnosis device for heart failure of this embodiment continuously observes one or more indexes including at least one of the following indexes; cardiac output, blood pressure, oxygen saturation in blood, (at least one of respiratory frequency, an index of respiratory stable and the amount of ventilation) or the arrhythmic state. And when significant changes have been found such as the occurrence of events including at least one of the following events (A) to (F), information on the number of occurrences of one or more events among these events, and a case where the total amount of time in which the events have occurred in a predetermined period exceeds a predetermined threshold value, or when a combination of above events or a combination with the fact of occurrence of other unmentioned events has occurred according to the predetermined rule, the device may be constituted so that the device generates alert signals and let the medical professional observe the changes. Alternatively, the device may be constituted to generate some kind of index values obtained by processing such information (for example, a physiological index itself or index indicating the degree of risk calculated according to the predetermined rule) and let the medical professional observe them.

The conditions under which the signal processing unit 22 and the determination unit 24 generate alert signals by observing changes in these physiological indexes, or generate index values indicating the risks are cases where, for example, at least one or more physiological indexes including either of cardiac output, blood pressure, oxygen saturation in blood, (at least one of respiratory frequency, an index indicating the respiratory stability and the amount of ventilation) or arrhythmia corresponds to one or more events including: (A) exceeding the predetermined upper limit threshold, (B) being less than the predetermined lower limit threshold, (C) exceeding the predetermined elevation limit threshold per predetermined time of period, (D) exceeding the predetermined decline limit threshold per predetermined time of period, (E) exceeding the predetermined elevation rate limit threshold, or (F) exceeding the predetermined decline rate limit threshold, or a case where a combination of these with the fact of occurrence of other unmentioned events has corresponded to a predetermined rule.

In addition, the device may be constituted to generate alert signals and index values indicating risks by using at least any of the occurrence of events (A) to (F), information about the duration of these events, information about the number of occurrences of one or more events from (A) to (F), the case where the total amount of time of occurrence of one or more events from (A) to (F) has exceeded a predetermined threshold within a predetermined time and the like.

Because changes in clinical conditions are often sudden and serious at this breakdown stage, the importance of the alert is higher compared to the functional stage of the compensatory mechanism 41.

A medical professional observes the generated alert signals and index values indicating risks, and takes necessary medical procedures such as hospitalization by performing diagnoses to confirm the results. Similarly to the former explanation, changes in types of drugs and dosage may be involved in this medical treatment.

Alternatively, when a patient and his or her family see alert signals and index values indicating the risks, they may respond to these events by going to a medical institution by themselves.

(3) A Rule Using Weighting of Each Physiological Index and a Rule Using Priority As a rule for generating index values indicating the generation of alert signals and risks at the stage when the compensatory mechanism is functioning or at the breakdown stage explained earlier, the rule may be made to follow a method for weighting each index value exemplified before.

Assuming a value indicating the degree of risk of index A, index B and index C according to the rule explained above is 100, 50, 10, respectively, and the weight of index A, B and C are equal, the comprehensive index value, for example, is 160 as they are simply added. However, suppose that the weighting of index A, index B and index C is 1, 5, and 10, respectively, and taking this into consideration, the comprehensive index is, for example, 28.1 according to calculation of 100×1/16+50×5/16+10×10/16.

In addition, as an alternative method, a rule in which each index has priority explained earlier may be used. For example, when determination is carried out by using respiratory frequency and blood pressure, a rule may be employed in which an alert signal is generated in the case where the respiratory frequency exceeds a predetermined elevation rate (elevation rate per unit period), even though the blood pressure is stable.

If these weightings and priority are made different between the first observation period in which the compensatory mechanism is functioning in order to improve various clinical conditions due to the fall of the heart pumping function in a patient and the second observation period in which the compensatory mechanism is suspected to be broken down, a high-precision diagnosis can be performed according to a characteristic physiological index of each stage.

Similarly, these weightings and priority may be made different according to at least any of the development stage of chronic heart failure, the severity of the diseases or background disease explained later. Such measure allows a precise diagnosis according to the clinical conditions of each patient.

(4) Selection of Each Physiological Index

As explained above, the diagnosis device of the present invention performs regulations such as generating alert signals indicating risks by using various physiological indexes, generating new indexes indicating risks during the period of the functional stage of the compensatory mechanism or the suspected observation period, the breakdown stage or the suspected observation period, or through each period.

Particularly, respiratory frequency, an index indicating respiratory stability, the amount of ventilation and the index indicating the augmentation state of the sympathetic nerve are important for a patient who is suspected to be at the functional stage of the compensatory mechanism.

In addition, respiratory frequency, an index indicating respiratory stability, the amount of ventilation and cardiac output are important for a patient who is at the breakdown stage of the compensatory mechanism.

From the above-mentioned findings by the present inventors, this invention may be constituted so that the selection of physiological indexes used by the present diagnosis device is different between the functional stage of the compensatory mechanism and the breakdown stage of the compensatory mechanism. For example, at the functional stage of the compensatory mechanism, the diagnosis device may be constituted so that physiological indexes are selected to include at least (at least one of respiratory frequency, an index indicating the respiratory stability and the amount of ventilation), and an index indicating the augmentation stage of the sympathetic nerve system. Furthermore, at the breakdown stage, the diagnosis device may be constituted to include at least (at least one of respiratory frequency, an index indicating the respiratory stability and the amount of ventilation) and cardiac output.

Alternatively, the diagnosis device may be constituted to include all of (at least one of respiratory frequency, an index indicating the respiratory stability and the amount of ventilation), the index indicating the augmentation stage of the sympathetic nerve system and cardiac output, and may be used as common indexes at each stage of heart failure by including additional indexes further or without. Or the device may be constituted so that weighting and priority are different, although the selection of indexes is the same between the stage of the compensatory mechanism and breakdown stage of the compensatory mechanism.

Furthermore, the device may be constituted so that the selection of each physiological index used for generating information for diagnosis, priority of each physiological index, and/or the weighting of each physiological index are made different depending on the progressive phase of chronic heart failure, severity and/or background diseases.

In addition, in the case where the same physiological indexes are used, there may be a case where the values of indexes required to make determination (the determination threshold) to generate alert signal are made different even in the same patient between the functional stage of the compensatory mechanism or the observation period of the suspected compensatory mechanism and the breakdown stage or the observation period of the suspected breakdown, as explained earlier, the device may be constituted to generate with high precision the diagnostic information at each stage by making the threshold values to make determination using index values different between stages of both periods.

Summing up the above statement, the diagnosis device in the present embodiment includes a constitution in which the physiological index, the order of priority, weighting or determination threshold used by the diagnosis device for evaluation (generation of information for diagnosis) are made different between the stage when the compensatory mechanism is functioning and the breakdown stage when the function is not working properly.

In addition, the diagnosis device of the present embodiment includes a constitution in which the selection of physiological index, the order of priority, weighting and the determination threshold used by the diagnosis device for evaluation (generation of information for diagnosis) are made different depending on at least one of the progressive phase of chronic heart failure, its severity, or the background diseases.

(5) Dealing with the Background of Individual Patients

For example, when the sympathetic nerve of patients with diabetes mellitus disease is disordered, the regulation cannot be performed precisely by using the augmentation state of sympathetic nerve C3 as an index, so the state C3 is preferably not used as an index.

Similarly, because the heart rate of a patient with atrial fibrillation cannot be accurately measured, a method may be adopted so that the heart rate is not used, its weighting is minimized, priority is lowered, or a different value is used for determination threshold of the index.

Similarly, because the heart rate of a patient with atrial fibrillation cannot be accurately measured, a method may be adopted so that the heart rate is not used as an index, its weighting is minimized, the order of priority is lowered, or a different value is used for determination threshold of the index.

Furthermore, for patients with respiratory disease, when the clinical condition is serious, the device is constituted so that determination is made based on the cardiac output P1, blood pressure P2 or pulse rate P9 instead of the respiratory frequency P8, the index indicating respiratory stability or the amount of ventilation. Or the device is constituted in such a way that, although at least any one of respiratory frequency P8, the respiratory stability or the amount ventilation is used as an index, its weighting is reduced, priority is reduced, or a different value is used for the determination threshold of the index.

Thus, the diagnosis device of the present embodiment can be constituted so that selection, weighting, priority, the determination threshold values using indexes and the like are made different based on patient's background medical conditions (background diseases of a patient).

In addition, dealing with other background diseases that are not exemplified is easily deduced from the findings about chronic heart failure by the present inventors explained earlier, and constitutions based on the above are also within the scope of the diagnosis device for heart failure of the present invention.

INDUSTRIAL APPLICABILITY

The diagnosis device of the present invention can be used, for example, in the manufacturing of medical or measuring devices for diagnosis (including medical equipment integrated therewith).

The invention claimed is:

1. A diagnosis device for providing information related to changes in clinical conditions of a patient having a chronic heart failure, the diagnosis device comprising:
   one or more detectors configured to continuously detect a plurality of physiological indexes of the patient that are different from each other, in a first observation period and in a second observation period; and
   a processor configured to:
      determine whether to generate the information for the patient according to the first observation period in which a compensatory mechanism of the patient is indicated as functioning or to the second observation period during which a breakdown of the compensatory mechanism is indicated, wherein the compensatory mechanism is a patient function which aims at improving the clinical conditions which deteriorate due to falling of a heart pumping function of the patient, and
      generate and output the information that a medical professional uses for at least one of an observation or a diagnosis of the patient, based on the plurality of physiological indexes,
   wherein the processor is further configured to generate the information so that at least one aspect of the following (1) to (4) aspects is made different between generating the information in the first observation period and generating the information in the second observation period:
      (1) a selection of physiological indexes among the plurality of physiological indexes to be used for the generating the information,
      (2) an order of priority of each of the selected physiological indexes used for the generating the information,
      (3) a weight for each of the selected physiological indexes, respectively, used for the generating the information, and
      (4) a determination threshold for each of the selected physiological indexes, respectively, used for the generating the information.

2. The diagnosis device according to claim 1, wherein the processor is further configured to select at least one of (a) an augmentation state of a sympathetic nervous system, (b) a state of a vasoconstriction, or (c) at least one of a respiratory frequency, an index indicating a respiratory stability, or an amount of a ventilation, of the patient, as at least one physiological index, among the plurality of physiological indexes, to be used for the generating the information during the first observation period.

3. The diagnosis device according to claim 1, wherein the processor is further configured to select at least one of (d) cardiac output, (e) blood pressure, (f) oxygen saturation in blood, (c) at least one of a respiratory frequency, an index indicating a respiratory stability, or an amount of a ventilation, or (g) an arrhythmic state, of the patient, as at least one physiological index, among the plurality of physiological indexes, to be used for the generating the information during the second observation period.

4. The diagnosis device according to claim 1, wherein the processor is further configured to generate the information based on at least one event among following (A) to (F) events related to at least one physiological index of the plurality of physiological indexes detected by the one or more detectors:
   (A) the at least one physiological index exceeding a predetermined upper limit threshold,
   (B) the at least one physiological index being less than a predetermined lower limit threshold,
   (C) the at least one physiological index exceeding a predetermined elevation limit threshold per a predetermined time,
   (D) the at least one physiological index exceeding a predetermined decline limit threshold per a predetermined time,
   (E) the at least one physiological index exceeding a predetermined elevation rate limit threshold, and
   (F) the at least one physiological index exceeding a predetermined decline rate limit threshold.

5. The diagnosis device according to claim 4, wherein the processor is further configured to, based on at least one piece of information about a period during which the at least one event occurred and continued, generate the information about a number of occurrences of the at least one event and a total amount of time during which the at least one event occurred and continued within a predetermined period.

6. A diagnosis device for providing information related to changes in clinical conditions of a patient having a chronic heart failure, the diagnosis device comprising:
   a processor configured to:
      based on the patient being in a state in which a compensatory mechanism of the patient is assumed to be functioning, generate and output the information for at least one of a prediction in an exacerbation of the patient or a diagnosis of the patient, based on information of a physiological index including at least one of (a) an augmentation state of a sympathetic nervous system, (b) a state of a vasoconstriction, or (c) at least one of a respiratory frequency, an index indicating a respiratory stability, or an amount of a ventilation, of the patient, wherein the compensatory mechanism of the patient is a patient function which aims at improving the clinical conditions which deteriorate due to falling of a heart pumping function of the patient.

7. The diagnosis device according to claim 6, wherein the processor is further configured to generate the information based on at least one event among following (A) to (F) events related to the physiological index:
   (A) the physiological index exceeding a predetermined upper limit threshold,
   (B) the physiological index being less than a predetermined lower limit threshold,
   (C) the physiological index exceeding a predetermined elevation limit threshold per a predetermined time,
   (D) the physiological index exceeding a predetermined decline limit threshold per a predetermined time,
   (E) the physiological index exceeding a predetermined elevation rate limit threshold, and
   (F) the physiological index exceeding a predetermined decline rate limit threshold.

8. The diagnosis device according to claim 7, wherein the processor is further configured to, based on at least one piece of information about a period during which the at least one event occurred and continued, generate the information about a number of occurrences of the at least one event, and a total amount of time during which the at least one event occurred and continued within a predetermined period.

9. A diagnosis device for providing information related to changes in clinical conditions of a patient having a chronic heart failure, the diagnosis device comprising:
   one or more detectors configured to continuously detect a plurality of physiological indexes of the patient that are different from each other; and
   a processor configured to generate and output the information that a medical professional uses for at least one of an observation or a diagnosis of the patient, based on the plurality of physiological indexes,
   wherein the processor is further configured to generate the information so that at least one aspect of following (1) to (4) aspects is made different according to one or more of a progressive stage of the chronic heart failure of the patient, a severity of the chronic heart failure of the patient, and background diseases of the patient:
     (1) a selection of physiological indexes among the plurality of physiological indexes to be used for the generating the information,
     (2) an order of priority of each of the selected physiological indexes used for the generating the information,
     (3) a weight for each of the selected physiological indexes, respectively, used for the generating the information, and
     (4) a determination threshold for each of the selected physiological indexes, respectively, used for the generating the information.

10. A diagnosis device for providing information related to changes in clinical conditions of a patient having a chronic heart failure, the diagnosis device comprising:
    a plurality of detectors configured to continuously detect a plurality of physiological indexes of the patient that are different from each other; and
    a processor configured to generate and output the information that a medical professional uses for at least one of an observation or a diagnosis of the patient, based on the plurality of physiological indexes,
    wherein the processor is further configured to generate the information based on the plurality of physiological indexes including at least one of (I) at least one of a respiratory frequency, an index indicating a respiratory stability, or an amount of ventilation of the patient, or (II) an index indicating an augmentation state of a sympathetic nervous system of the patient.

11. The diagnosis device according to claim 10, wherein the processor is further configured to generate the information for the patient whose compensatory mechanism is assumed to be functioning,
    wherein the compensatory mechanism is a patient function which aims at improving the clinical conditions which deteriorate due to falling of a heart pumping function, of the patient.

12. The diagnosis device according to claim 10, wherein the index indicating the augmentation state of the sympathetic nervous system comprises one or more indexes selected from a group consisting of a heart rate variable (HRV), a pulse rate, a blood pressure, and a vasoconstriction, of the patient.

13. A diagnosis device for providing information related to changes in clinical conditions of a patient having a chronic heart failure, the diagnosis device comprising:
    a plurality of detectors configured to continuously detect a plurality of physiological indexes of the patient that are different from each other; and
    a processor configured to generate and output the information that a medical professional uses for at least one of an observation or a diagnosis of the patient, based on the plurality of physiological indexes,
    wherein the processor is further configured to generate the information based on the plurality of physiological indexes including at least one of (I) at least one of a respiratory frequency, an index indicating a respiratory stability, or an amount of a ventilation, of the patient, or (II) a cardiac output of the patient.

14. The diagnosis device according to claim 13, wherein the processor is further configured to generate the information for the patient who is in a breakdown stage of a compensatory mechanism of the patient,
    wherein the compensatory mechanism is a patient function which aims at improving the clinical conditions which deteriorate due to falling of a heart pumping function, of the patient.

15. A diagnosis device for providing information related to changes in clinical conditions of a patient having a chronic heart failure, the diagnosis device comprising:
    a plurality of detectors configured to continuously detect a plurality of physiological indexes of the patient that are different from each other; and
    a processor configured to generate and output the information that a medical professional uses for at least one of an observation or a diagnosis of the patient, based on the plurality of physiological indexes,
    wherein the processor is further configured to generate the information based on the plurality of physiological indexes including at least one of (I) at least one of a respiratory frequency, an index indicating a respiratory stability, or an amount of a ventilation, of the patient, (II) an index indicating an augmentation state of a sympathetic nervous system of the patient, or (III) a cardiac output of the patient.

* * * * *